United States Patent
Yonehara et al.

Patent Number: 5,985,591
Date of Patent: Nov. 16, 1999

[54] METHOD FOR THE DETERMINATION OF GLYCOSYLATED PROTEINS

[75] Inventors: Satoshi Yonehara; Tsuguki Komori, both of Osaka, Japan

[73] Assignee: Kyoto Daiichi Kagaku Co., Ltd., Kyoto, Japan

[21] Appl. No.: 09/196,663

[22] Filed: Nov. 19, 1998

[30] Foreign Application Priority Data

Nov. 26, 1997 [JP] Japan ................................ 9-324732

[51] Int. Cl.$^6$ .............................. C12Q 1/28; C12Q 1/37; C12Q 1/00
[52] U.S. Cl. .................................. 435/28; 435/23; 435/4
[58] Field of Search ..................... 435/28, 23, 4

[56] References Cited

U.S. PATENT DOCUMENTS

| | | | |
|---|---|---|---|
| 5,370,990 | 12/1994 | Staniford et al. | 435/4 |
| 5,639,672 | 6/1997 | Burd et al. | 435/4 |

FOREIGN PATENT DOCUMENTS

| | | |
|---|---|---|
| 61-268178 | 11/1986 | Japan . |
| 61-280297 | 12/1986 | Japan . |
| 3-155780 | 7/1991 | Japan . |
| 6-046846 | 2/1994 | Japan . |
| 7-289253 | 11/1995 | Japan . |
| WO 96/34977 | 11/1996 | WIPO . |

OTHER PUBLICATIONS

The Journal of Biological Chemistry vol. 239, No. 11, Nov. 1964, p. 3790–3796, Sangduk Kim et al., "Purification and Properties of the Enzyme".

*Primary Examiner*—Louise N. Leary
*Attorney, Agent, or Firm*—Merchant & Gould P.C.

[57] ABSTRACT

A method for measuring the amount of glycosylated protein comprising the steps of decomposing glycosylated proteins with protease, causing a redox reaction between the decomposed products and an Amadori compound oxidoreductase, and determining the redox reaction so as to measure the amount of glycosylated proteins, wherein the decomposition with the protease is carried out in the presence of at least one substrate selected from the group consisting of metalloporphyrin, cytochrome and diaphorase.

10 Claims, 3 Drawing Sheets

METHOD FOR THE DETERMINATION OF GLYCOSYLATED PROTEINS

FIELD OF THE INVENTION

The present invention relates to a method for measuring the amount of glycosylated proteins in a sample by an enzymatic method.

BACKGROUND OF THE INVENTION

Glycosylated proteins (e.g. glycosylated albumin) in blood consist of glucose and blood protein (e.g. albumin) bonded by non-enzymatic covalent bonds. Aldehyde groups of glucose and amino groups of protein are responsible for the covalent bonds. Glycosylated albumin or the like in blood reflects the blood sugar level of a certain period in the past. Consequently, the measured value of glycosylated albumin has recently been noted as an important index for diagnosis and observation of conditions of diabetes.

Examples of the methods for measuring the amount of glycosylated proteins include high-performance liquid chromatography (HPLC) method, immunoassay, chemical method (NBT test), dye-binding methods, enzymatic methods, and the like. Above all, the enzymatic method employing an Amadori compound oxidoreductase such as fructosyl amino acid oxidase (FAOD) makes it possible to measure the amount of glycosylated proteins more accurately and promptly than the other methods.

The method for measuring the amount of glycosylated proteins by the use of FAOD is performed as follows. First, the glycosylated proteins are treated with protease so as to decompose them into peptides or amino acids, because FAOD acts with difficulty on large proteins or long peptides. Then, the decomposed products are treated with FAOD.

Thus, by measuring the amount of hydrogen peroxide produced by the treatment with FAOD by electric method or enzymatic method, the concentration of glycosylated protein can be determined.

As the enzymatic method for measuring the hydrogen peroxide, there is, for example, a method in which peroxidase (POD) and a substrate generating color by oxidation are used to determine the degree of color generation of the substrate.

In the method for measuring the amount of glycosylated proteins by the enzymatic method, there is a problem in that even if the glycosylated proteins are treated with protease beforehand, short peptides capable of being a substrate for an Amadori compound oxidoreductase cannot sufficiently be produced. In particular, protease acts only with difficulty on glycosylated proteins contained in blood. In order to avoid this problem, an improvement method has been suggested in which glycosylated proteins are treated with protease in the presence of POD before the treatment with the oxidoreductase (WO 96/34977). According to this improvement method, the short peptides capable of being the above-mentioned substrate can be produced effectively. Moreover, it is not clear why the glycosylated proteins are well decomposed if they coexist with POD during the treatment with protease.

However, this improvement method has the following problem. Since POD itself is a glycosylated protein and decomposed with protease to produce a substrate for the oxidoreductase, the results of the method are less reliable.

SUMMARY OF THE INVENTION

It is therefore an object of the present invention to provide a method for measuring the amount of glycosylated proteins in which highly reliable measured values can be obtained.

In order to achieve the above-mentioned object, the method for measuring the amount of glycosylated proteins of the present invention comprises the steps of decomposing glycosylated proteins in a sample with protease, causing a redox reaction between the decomposed products and an Amadori compound oxidoreductase, and determining the redox reaction so as to measure the amount of glycosylated proteins. In the method, the decomposition with protease is carried out in the presence of at least one substance selected from the group consisting of metalloporphyrin, cytochrome and diaphorase.

In other words, according to the method of the present invention, by carrying out the decomposition of glycosylated protein with protease in the presence of the predetermined substances in place of POD, the decomposition of glycosylated protein is promoted. Since these substances are not glycosylated proteins, even if they are subjected to decomposition with protease, substrates for the Amadori compound oxidoreductase are not produced, and, therefor, its redox reaction is not affected.

In the present invention, the metalloporphyrin is a chelate compound of porphyrin and a metal ion. Specifically, it is a chelate compound of metal ion such as $Fe^{2+}$, $Mg^{2+}$, $Co^{2+}$, $Mn^{2+}$, and the like and porphyrin. Examples of the porphyrin include hemin and the like. Examples of the cytochrome include cytochrome a, cytochrome b, cytochrome c, and the like. The diaphorase has another name, dihydropolyamide dehydrogenase. These three kinds of substances may be used singly or in combinations of two or more of them.

The method of the present invention is carried out as follows. For example, the redox reaction with the Amadori compound oxidoreductase is performed at the same time as or after the decomposition treatment. Thereafter, the amount of hydrogen peroxide produced by the redox reaction or the amount of oxygen consumed by the redox reaction is measured, and thereby the amount of glycosylated proteins can be determined by using a calibration equation or a calibration curve, etc. The method for measuring the amount of hydrogen peroxide or the amount of oxygen is not particularly limited, and any conventionally known method may be employed. Moreover, the measurement of the amount of glycosylated proteins of the present invention includes the measurement of the concentration of glycosylated protein.

In the method of the present invention, it is preferable that the glycosylated protein is glycosylated albumin and for glycosylated globulin. This is advantageous because these glycosylated proteins are index substances for diagnosis or observation of diabetes.

DETAILED DESCRIPTION OF THE INVENTION

Figure 1:
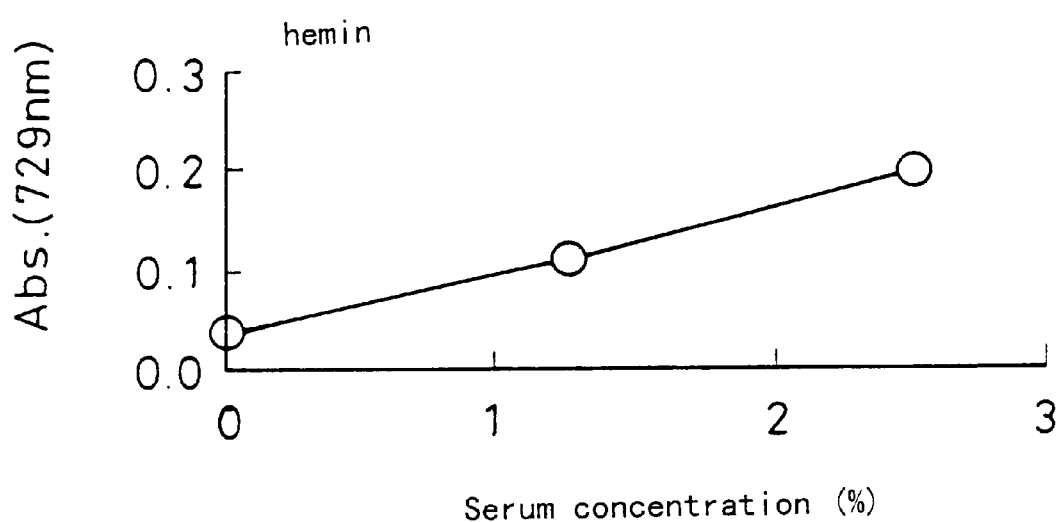
FIG. 1 is a graph showing the relationship between the serum concentration and the absorbance when using hemin in one embodiment of the present invention.

Next, the present invention will be described in detail.

The method of the present invention comprises, for example, three steps, i.e. a first step of decomposing glycosylated proteins with protease, a second step of causing a redox reaction between the protease treated products and an Amadori compound oxidoreductase, and a third step of determining the above-mentioned redox reaction of the Amadori compound oxidoreductase. These steps may be carried out separately. However, as mentioned below, the step of causing the redox reaction and the step of determining the redox reaction may be carried out simultaneously.

Glycosylated proteins to be analyzed of the present invention are not particularly limited, and the examples include glycosylated albumin, glycosylated globulin, glycosylated hemoglobin, glycosylated casein, and the like. Furthermore, examples of samples to be analyzed of the present invention include blood, serum, plasma, milk, brewed food such as bean paste, soy source, or the like.

The type of the protease used for the protease treatment is not particularly limited. For example, protease K, subtilisin, trypsin and aminopeptidase, or the like can be used. Furthermore, the protease treatment is preferably carried out in a buffer solution. The condition is appropriately decided in accordance with the type of the protease to be used, the type or the concentration of the glycosylated protein, or the like. For example, in a case where serum is treated with protease K, the protease concentration in the reaction solution may be 0.2–1 weight %, the serum concentration in reaction solution 1–10 volume %, the reaction temperature 20–50° C., the reaction time 50–120 minutes, and pH 6 to 9. Also, the type of the buffer solution is not particularly limited and examples include tris hydrochloric acid buffer solution, EPPS buffer solution, PIPES buffer solution, and the like.

Furthermore, this protease treatment is carried out in the presence of at least one selected from the group consisting of metalloporphyrin, cytochrome and diaphorase. The concentrations of these substances in the reaction solution are appropriately decided in accordance with the types or the like.

The decomposed products obtained by the protease treatment are subjected to treatment with an Amadori compound oxidoreductase. In this treatment, the enzyme catalyzes the reaction represented by the following chemical formula (1), in which $R^1$ denotes aldose residue of sugar, and $R^2$ denotes protein, peptide or amino acid residue.

(chemical formula 1)

$$R^1—CO—CH_2—NH—R^2+O_2+H_2O$$
$$\rightarrow R^1—CO—CHO+R^2—NH_2+H_2O_2$$

The Amadori compound oxidoreductase for catalyzing the above-mentioned reaction may be, for example, an enzyme as mentioned below. FAOD is preferably used, and FAOD described in (6) is more preferably used.

(1) FAOD derived from bacteria of the genus Corynebacterium (JP-B 6-65300 and JP-B 5-33997)
(2) FAOD derived from bacteria of the genus Aspergillus (JP-A 3-155780)
(3) ketoamine oxidase derived from bacteria of the genus Corynebacterium, Fusarium, Acremonium or Debraryomyces (JP-A 5-192193)
(4) fructosyl amine deglycase derived from bacteria of the genus Candida (JP-A 6-46846)
(5) alkyl lysinase (J. Biol. Chem. Vol. 239, pp 3790–3796, 1964)
(6) FAOD described in JP-A 7-289253

It is preferable that this treatment is performed in a buffer solution. The treatment condition is appropriately decided depending on the concentration, etc. of the above-mentioned decomposed products. Also, the type of the buffer solution is not particularly limited, and examples include tris hydrochloric acid buffer solution, EPPS buffer solution, PIPES buffer solution, and the like.

Next, the redox reaction by the above-mentioned enzyme is determined. In general, since this reaction is performed in the presence of water and oxygen, oxygen is consumed and hydrogen peroxide is produced in this reaction as shown in the above chemical formula (1). Consequently, by measuring the concentration of the hydrogen peroxide or the concentration of the oxygen, the redox reaction can be determined.

Examples of the method for determining the redox reaction by measuring the concentration of hydrogen peroxide include a method using peroxidase (POD) and a substrate producing the detectable products. Example of such substrates include substrates that generate color by oxidation (hereinafter, "a color-generating substrate" will be referred to). Examples of such a substrate include orthophenylenediamine (OPD, the wavelength of absorbed light is 492 nm), the combination of Trinder's Reagent and 4-aminoantipyrine, DA-64, and the like. In a case where these color-generating substrates are used, the concentration of hydrogen peroxide can be determined by measuring the light absorbance of the reaction solution by means of spectrophotometer. In addition, if the calibration curve or calibration equation is prepared beforehand, the concentration of glycosylated protein can be calculated from the concentration of hydrogen peroxide.

Furthermore, it is preferable that the treatment with POD is carried out in a buffer solution under the usual conditions where POD concentration in the reaction solution is 1–10000 U/l, the concentration of the color-generating substrate is 0.1–5 mmol/l at 20 to 37° C. for 1 to 5 minutes, and the pH of the redox solution is 6 to 9. The type of the buffer solution includes, for example, tris hydrochloric acid buffer solution, EPPS buffer solution, PIPES buffer solution, and the like.

In the method of the present invention, the above-mentioned three steps may be carried out separately. However, as shown below, where hydrogen peroxide is determined with POD, the redox reaction with the Amadori compound and the treatment with POD may be carried out simultaneously.

In other words, the reaction is performed by adding the Amadori compound oxidoreductase, POD and the color-generating substrate into the buffer solution containing the products treated with protease for a constant period. Thereafter, the absorbance is determined. In addition, it is also possible to perform the treatment with protease and the redox reaction with the above-mentioned oxidoreductase simultaneously.

The present invention will be explained below by way of Examples. In the following Examples, FLOD-S described in Publication of Japanese Patent Application (Tokkai Hei) No. 7-289253 was used as the FAOD. The above-mentioned FLOD-S is fructosyl amino acid oxidase, which effects specifically on at least one of fructosyl lysine and fructosyl-N'—Z— lysine (FNZ) and is derived from the *Fusarium oxysporum* S-1F4 (FERM BP-5010). This FLOD-S was prepared by the following procedure.

Preparation of FLOD-S *Fusarium oxysporum* S-1F4: FERM B P-5010 was inoculated into a 10 L of culture medium (pH 6.0) containing 0.5% FZL, 1.0% glucose, 0.1% dipotassium phosphate, 0.1% monosodium phosphate, 0.05% magnesium sulfate, 0.01% calcium chloride and 0.2% yeast extract, stirred and cultured in a jar fermenter at a ventilation volume of 2 L/minutes, at a stirring speed of 400 rpm, and at 28° C. for 24 hours. The culture was collected by filtration. A part of the mycelium (200 g) was suspended in 0.1 M tris hydrochloric acid buffer solution (pH 8.5) containing 2 mM DTT and was ground with Dino-Mill. The ground solution was centrifuged at 10,000 rpm for 15 minutes. The obtained solution was defined as a crude enzyme solution (cell-free extract). Ammonium sulfate was added into the crude enzyme solution to 40% saturation, stirred and centrifuged at 12,000 rpm for 10 minutes. Ammonium sulfate was added into the obtained supernatant to 75% saturation, stirred and centrifuged at 12,000 rpm for 10 minutes. The precipitate was dissolved in 50 mM tris hydrochloric acid buffer solution (pH8.5) containing 2 mM DTT (hereinafter "buffer solution A"), and dialyzed in the buffer solution A overnight. The dialysate was adsorbed on the DEAE-Sephacel column which had been balanced with the buffer solution A, washed with the buffer solution A, and then eluted by 0–0.5 M potassium chloride linear concentration gradient. Active fractions were collected and fractionated with 55–75% ammonium sulfate solution and, dialyzed with the buffer solution A overnight. Ammonium sulfate was added into the dyalysate to 25% saturation, adsorbed on the phenyl-Toyopearl column that had been balanced with the buffer solution A containing 25% saturated ammonium sulfate, washed with the buffer solution, and then eluted by linear concentration gradient of the 25–0% ammonium sulfate solution. Active fractions were collected, ammonium sulfate added to 40% saturation, and adsorbed on the butyl-Toyopearl column that had been balanced with the buffer solution A containing 40% saturation ammonium sulfate, washed with the buffer solution and then eluted by linear concentration gradient of 40–0% ammonium sulfate solution. Active fractions were collected, ammonium sulfate added to 80% saturation, stirred, and centrifuged at 12,000 rpm for 10 minutes. The obtained precipitate was dissolved in 0.1 M buffer solution A Active fractions were collected from the precipitate solution with gel filtration chromatography (Sephacryl S-200) which had been balanced with 0.1 M buffer solution A containing 0.1 M potassium chloride, and concentrated by ultrafiltration. Purified enzyme (30–60 units) was obtained from the concentrate by the treatment with Pharmacea FPLC system. This treatment was carried out by using Mono Q column and eluting with linear concentration gradient of buffer solution A containing 0–0.5 M potassium chloride.

EXAMPLE 1

We treated serum collected from healthy human adult subjects with protease (manufactured by SHIN NIHON CHEMICAL CO., LTD. and marketed under the trade name of SUMIZYME MP) at 37° C. for 2 hours. The serum concentrations were 0 (v/v) %, 1.25 (v/v) %, and 2.5 (v/v) %; the hemin concentration was 0.01 (w/v) %. Furthermore, in this and other examples, as the buffer solution, we used 200 mmol/l tris hydrochloric acid buffer solution (pH 8.0). Furthermore, unless otherwise noted, we used purified water for the solvent.

The composition of the reaction solution are described below

| | |
|---|---|
| serum solution | 0.05 ml |
| buffer solution | 0.55 ml |
| hemin (manufactured by Sigma Chemical Co) | 0.20 ml |
| 1% protease solution (solvent: buffer solution) | 0.30 ml |
| 30 mmol/l hydrogen peroxide solution | 0.10 ml |

Next, we prepared a mixed solution of POD and color-generating substrate by dissolving 0.29 mmol/l color-generating substrate (DA-64 manufactured by Wako Pure Chemical Industries, LTD) and 29 KU/l POD into the buffer solution. Next, we performed the FAOD treatment at 25° C. for 5 minutes by adding 0.7 ml of the mixed solution and 0.10 ml of FAOD solution (100 KU/l, solvent: buffer solution) into the above-mentioned protease treated products (solution).

Then, we measured the absorbance of the reaction solution at 726 nm with spectrophotometer. The graph of FIG. 1 shows the results.

As can be seen from the graph of FIG. 1, the absorbance was increased, as the serum concentration was increased.

EXAMPLE 2

We performed the same treatment and operation as Example 1 except that we used 0.5 (w/v) % cytochrome c in place of hemin, and measured the absorbance. The graph of FIG. 2 shows the results.

Figure 2:
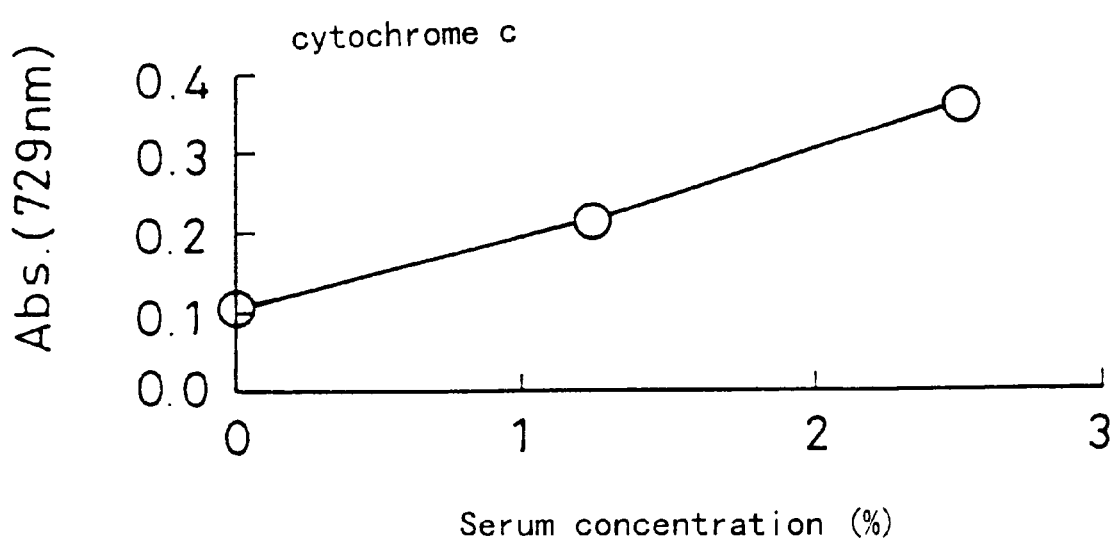
FIG. 2 is a graph showing the relationship between the serum concentration and the absorbance when using cytochrome c in one embodiment of the present invention.

As can be seen from the graph of FIG. 2, the absorbance was increased, as serum concentration was increased.

EXAMPLE 3

We performed the same treatment and operation as Example 1 except that we used two different kinds of diaphorase, i.e. 0.5 (w/v) % diaphorase and 1.0 (w/v) % diaphorase in place of hemin, and measured the absorbance. The graph of FIG. 3 shows the results.

Figure 3:
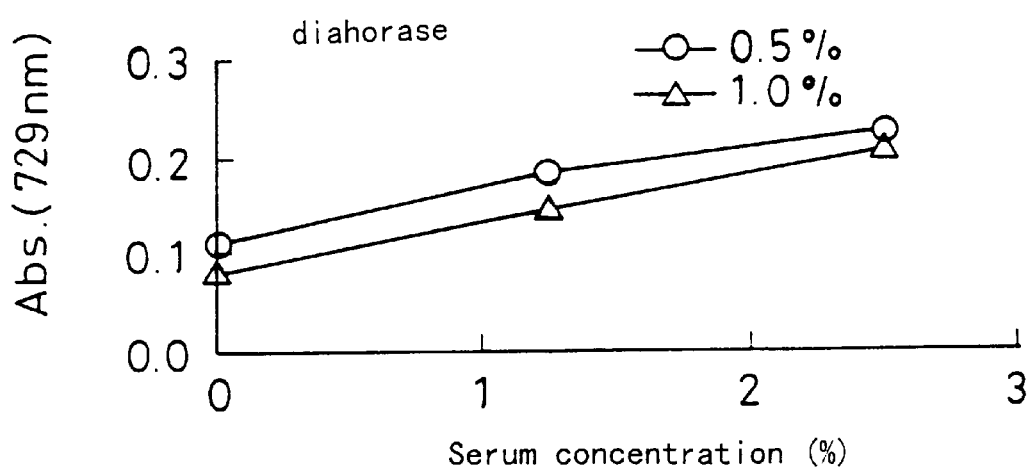
FIG. 3 is a graph showing the relationship between the serum concentration and the absorbance when using diaphorase in one embodiment of the present invention.

As can be seen from the graph of FIG. 3, the absorbance was increased, as the serum concentration was increased.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A method for measuring the amount of glycosylated protein comprising the steps of decomposing glycosylated proteins in a sample with protease, causing a redox reaction between the decomposed products and an Amadori compound oxidoreductase, and determining the redox reaction so as to measure the amount of glycosylated proteins, wherein the decomposition with the protease is carried out in the presence of at least one substance selected from the group consisting of metalloporphyrin, cytochrome and diaphorase.

2. The method according to claim 1, wherein the metalloporphyrin is a chelate compound of a bivalent metal ion and porphyrin.

3. The method according to claim 2, wherein the bivalent metal ion is at least one selected from the group consisting of $Fe^{2+}$, $Mg^{2+}$, $Co^{2+}$ and $Mn^{2+}$.

4. The method according to claim 1, wherein the cytochrome is at least one selected from the group consisting of cytochrome a, cytochrome b and cytochrome c.

5. The method according to claim 1, wherein the redox reaction is determined by measuring the amount of hydrogen peroxide produced by the redox reaction or measuring the amount of oxygen consumed by the redox reaction.

6. The method according to claim 5, wherein the measuring the amount of hydrogen peroxide uses peroxidase and a substrate generating color by oxidation.

7. The method according to claim 6, wherein the substrate generating color is orthophenylenediamine.

8. The method according to claim 1, wherein the treatment with protease and the reaction of the Amadori compound oxidoreductase are carried out simultaneously.

9. The method according to claim 6, wherein the reaction of the Amadori compound oxidoreductase and the reaction of peroxidase are carried out simultaneously.

10. The method according to claim 1, wherein the Amadori compound oxidoreductase is fructosyl amino acid oxidase (FAOD).

* * * * *